United States Patent
Harlin et al.

(10) Patent No.: US 8,957,269 B2
(45) Date of Patent: Feb. 17, 2015

(54) METHOD FOR PRODUCING OLEFINIC MONOMERS FROM BIO OIL

(75) Inventors: Ali Harlin, Kerava (FI); Tapani Penttinen, Huutjärvi (FI); Jari Räsänen, Imatra (FI); Olli Aaltonen, Helsinki (FI)

(73) Assignee: Stora Enso Oyj, Helsinki (FI)

( * ) Notice: Subject to any disclaimer, the term of this patent is extended or adjusted under 35 U.S.C. 154(b) by 225 days.

(21) Appl. No.: 13/146,857

(22) PCT Filed: Jan. 29, 2010

(86) PCT No.: PCT/FI2010/050051
§ 371 (c)(1),
(2), (4) Date: Nov. 10, 2011

(87) PCT Pub. No.: WO2010/086507
PCT Pub. Date: Aug. 5, 2010

(65) Prior Publication Data
US 2012/0053379 A1    Mar. 1, 2012

(30) Foreign Application Priority Data

Jan. 29, 2009   (FI) ..................... 20095079

(51) Int. Cl.
*C10G 11/02* (2006.01)
*C10G 51/02* (2006.01)
(Continued)

(52) U.S. Cl.
CPC ............... *C10G 51/02* (2013.01); *C07C 11/02* (2013.01); *C07C 11/04* (2013.01); *C07C 11/06* (2013.01);
(Continued)

(58) Field of Classification Search
CPC ... C10G 3/40; C10G 3/42–3/49; C10G 11/00; C10G 11/02; C10G 11/04; C10G 11/05; C10G 55/00; C10G 55/02; C10G 55/06; C07C 11/02; C07C 11/04; C07C 11/06
USPC .......... 585/330, 240–242, 639, 733; 44/306–308, 605, 606; 208/106
See application file for complete search history.

(56) References Cited

U.S. PATENT DOCUMENTS 5,493,037 A * 2/1996 Henderson .................... 554/147
5,705,722 A    1/1998 Monnier et al.
(Continued)

FOREIGN PATENT DOCUMENTS

CN    101314718 A    12/2008
WO    WO 2008/101945 A1    8/2008
(Continued)

OTHER PUBLICATIONS

International Search Report for PCT/FI2010/050051 dated May 10, 2010.
(Continued)

*Primary Examiner* — In Suk Bullock
*Assistant Examiner* — Philip Louie
(74) *Attorney, Agent, or Firm* — Birch, Stewart, Kolasch & Birch, LLP

(57) ABSTRACT

The invention relates to a method of producing olefinic monomers for the production of a polymer. The invention particularly relates to the production of tall oil-based biopolymers, such as polyolefins. In the stages of the method
  bio oil, with a content of over 50% of fatty acids of tall oil and no more than 25% of resin acids of tall oil, and hydrogen gas are fed into a catalyst bed (7);
  the oil is catalytically deoxygenated in the bed by hydrogen;
  the flow exiting the bed is cooled down and divided into a hydrocarbon-bearing liquid phase (10) and a gas phase; and
  the hydrocarbon-bearing liquid (13) is subjected to steam cracking (4) to provide a product containing polymerizing olefins.

The deoxygenation in the bed can be followed by a catalytic cracking or, with a suitable catalyst, the deoxygenation and cracking can be simultaneous. The separated hydrogen-bearing gas phase can be circulated in the process.

15 Claims, 1 Drawing Sheet

(51) Int. Cl.
*C07C 11/02* (2006.01)
*C07C 11/04* (2006.01)
*C07C 11/06* (2006.01)
*C10G 9/00* (2006.01)
*C10G 3/00* (2006.01)
*C10G 9/36* (2006.01)

(52) U.S. Cl.
CPC ..... *C10G 9/00* (2013.01); *C10G 11/02* (2013.01); *C10G 3/46* (2013.01); *C10G 3/50* (2013.01); *C10G 3/54* (2013.01); *C10G 9/36* (2013.01); *C10G 2300/1014* (2013.01); *C10G 2400/20* (2013.01); *C10G 2300/807* (2013.01)
USPC ........... 585/330; 585/240; 585/241; 585/242; 585/639; 585/733; 44/306; 44/307; 44/308; 44/605; 44/606

(56) References Cited

U.S. PATENT DOCUMENTS

| | | |
|---|---|---|
| 2006/0207166 A1* | 9/2006 | Herskowitz et al. ............ 44/385 |
| 2007/0006523 A1* | 1/2007 | Myllyoja et al. ................ 44/308 |
| 2007/0090019 A1* | 4/2007 | Keusenkothen et al. ..... 208/106 |
| 2008/0308458 A1* | 12/2008 | Dindi et al. ................... 208/137 |
| 2010/0292517 A1 | 11/2010 | Debuisschert et al. |

FOREIGN PATENT DOCUMENTS

| | | |
|---|---|---|
| WO | WO 2008/127956 A1 | 10/2008 |
| WO | WO 2009/004181 A2 | 1/2009 |

OTHER PUBLICATIONS

Written Opinion, PCT/ISA/237, PCT/FI2010/050051 dated May 10, 2010.

\* cited by examiner

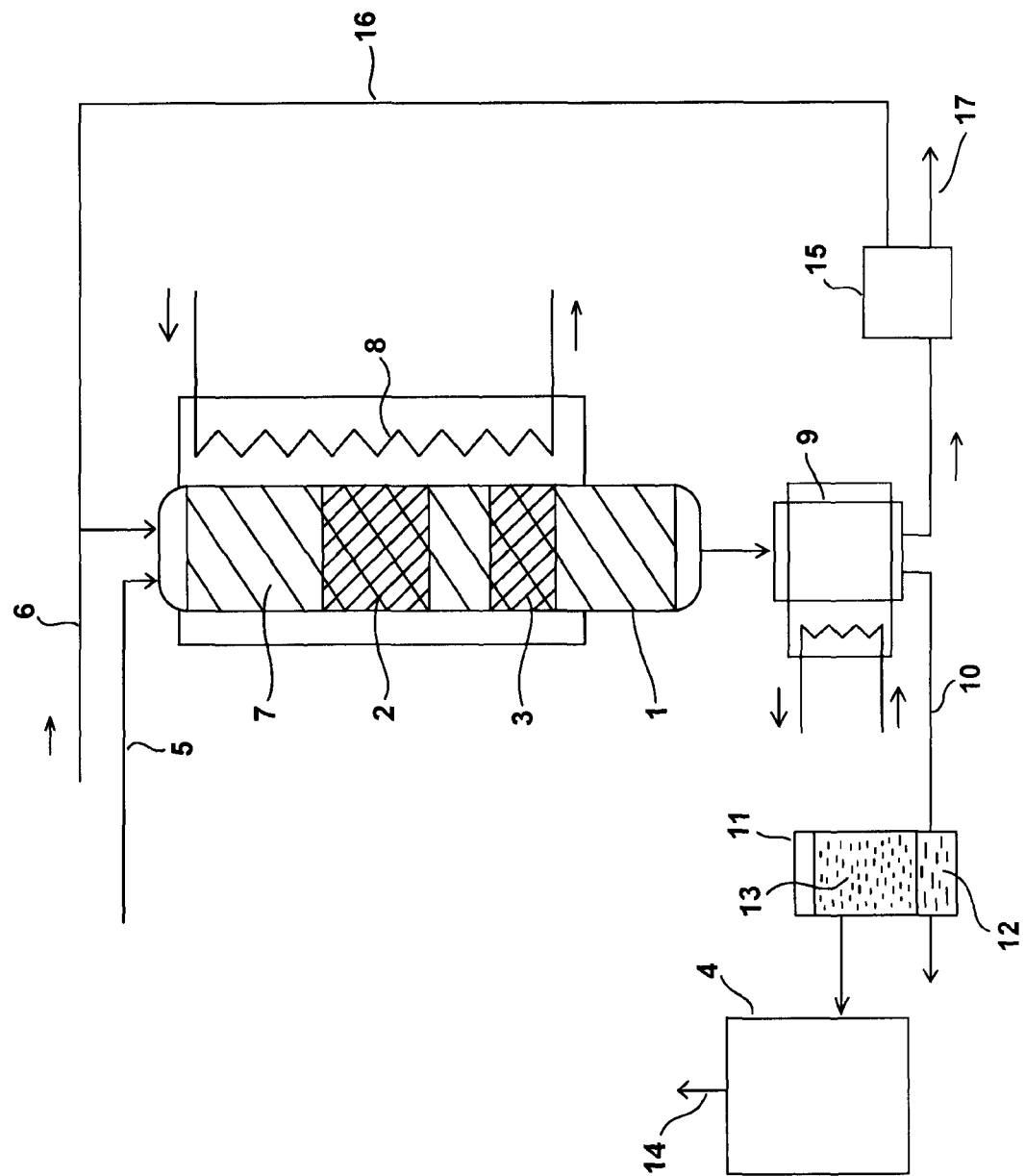

METHOD FOR PRODUCING OLEFINIC MONOMERS FROM BIO OIL

The invention relates to a method of producing olefinic monomers for the preparation of a biopolymer.

The conventional raw material for the preparation of polyolefins, such as polyethylene and polypropylene, comprises crude oil. Hydrocarbon fractions, which contain alkanes and are obtained from the fractional distillation of crude oil, have been cracked by steam at high temperatures into alkanes that have shorter chains and alkenes, such as ethylene and propylene, which are source materials for the preparation of polyethylene and polypropylene.

As a substitutive alternative for fossil raw materials, sources of renewable organic materials have been explored for the preparation of polymers. It has been suggested that polymers be prepared, e.g., of maize or sugar; however, a disadvantage with this is that the polymer production then has to compete for the same raw materials with food production, the resources of which are globally limited. An ideal source of raw material would comprise wood, its reserves being abundant and it having no use in food production.

Cracking a wood-based material into a naphtha boiling point range liquid is described in the patent specification WO2008/039756. The starting material of the process comprises waste cellulose or lignin, which is elutriated in tall oil that functions as a liquid carrier. According to the specification, the slurry is subjected to a catalytic hydrocracking process, the metal, such as Ni and Mo, in its catalyst being combined with a zeolite or silica alumina catalyst. As suitable reactors, the specification mentions slurry and fluidized bed reactors, even though an autoclave reactor is used in an exemplary embodiment. According to the specification, the product is obtained as steam, which is condensed into liquid, and any excess hydrogen can be circulated in the process. The excess liquid, which contains the used catalyst, is cleaned and circulated to the slurry that is fed into the process. As a result of cracking, oxygen is removed from the product and molecules are cracked into smaller ones. The general objects of the specification comprise the production of fuels and chemical intermediate products; also monomers for the production of plastics are mentioned. However, all of the more specific descriptions of the use of the hydrocracked liquid product for such purposes are lacking from the specification.

The specification US-2004/0 230 085 discloses the catalytic hydrodeoxygenation of the fatty acids of tall oil as part of the production of a bio-based diesel fuel. The deoxygenation is effected by gaseous hydrogen in a catalyst bed, which comprises a metal catalyst, such as NiMO or CoMo, and the carrier comprises alumina and/or silica. The oxides of carbon and various impurities are separated from the gaseous mixture generated at the deoxygenating stage and the purified hydrogen is circulated back to the process. At the second stage of the process, the liquid phase is subjected to isomerization that renders the product suitable for use as a fuel. As the isomerization stage is sensitive to aromatic and naphthene impurities, the resin acids of tall oil that can be generated in the deoxygenation are removed from the starting material as effectively as possible. In Example 1 of the specification, the amount of resin acids among the fatty acids was 1.9%.

The specification US-2008/0 154 073 discloses a similar process for the production of diesel fuel from biorenewable feedstock, such as vegetable oil. Tall oil is mentioned as a possible raw material, containing resin acids in addition to fatty acids; however, according to test results, the tall oil produced a considerable portion of hydrocarbon fractions heavier than diesel, in contrast to the soy oil that was also used in the tests.

The specification US-2007/0 135 669 also describes the production of diesel fuel from biorenewable feedstocks and observes the unwanted presence of unsaturated and aromatic hydrocarbons in the end product. The specification describes as the invention a process wherein the fatty acids distilled from tall oil are first isomerized and, thereafter, deoxygenated at the second stage of the process.

BRIEF DESCRIPTION OF THE DRAWINGS

FIG. 1 shows schematically an apparatus intended for the application of the invention.

The purpose of the present invention is to provide an industrially useful process, which can be used to convert wood-based raw material into olefinic monomers that are suitable for the production of biopolymer. Thus, the production of polymer can be based on renewable biological raw material sources. The method according to the invention essentially consists of the following stages:

bio oil, with a content of over 50% of fatty acids of tall oil and no more than 25% of resin acids of tall oil, and hydrogen gas are fed into a catalyst bed;

the oil is catalytically deoxygenated in the bed by hydrogen;

the flow exiting the bed is cooled down and divided into a hydrocarbon-bearing liquid phase and a gas phase; and the hydrocarbon-bearing liquid is subjected to steam cracking to provide a product containing polymerizing olefins.

The starting oil material can be purely tall oil-based, consisting of at least 75% of fatty acids of tall oil and no more than 25% of fatty acids of tall oil. Such acid mixtures can be separated from crude tall oil by distillation. The olefinic monomers that are obtained as the end product of the process of the invention can be converted into a biopolymer that is exclusively based on the renewable raw material source.

It is also possible to blend the tall oil components in the starting material with other suitable bio oils, such as vegetable oils, e.g., palm oil.

The tall oil in the invention refers to the oil product that is obtained not only from pine (pinus), but also from other softwood trees and consists of fatty and resin acids or their esters.

The invention is based on the fact that the hydrodeoxygenation of the fatty acids of tall oil, which is carried out by a method known as such, produces a hydrocarbon mixture, which can be further processed by steam cracking to form low-molecular olefins without the problems caused by the fairly small fractions of aromatic or unsaturated aliphatic or cyclic hydrocarbons. As steam cracking comprises technology that belongs to normal petrochemistry, it is easy to implement the process according to the invention in practice.

As the process according to the invention is more insensitive to the presence of the said components than the manufacture of diesel fuel, the resin acids of tall oil do not need to be separated from the fatty acids as carefully. However, as there are other advantageous end uses for the resin acids, it would be worthwhile to stress the composition of the starting material on the fatty acids of tall oil, oleic acid and linoleic acid. The amount of resin acids in the starting material is about 25% at the most, but regarding the economy of the process, their portion is preferably within 2-5%.

The catalytic hydrodeoxygenation acts by releasing oxygen from the fatty acids and forming water, carbon monoxide and/or carbon dioxide. Considerable breaking of carbon chains into smaller molecules does not take place yet. In the invention, exploiting a catalytic fixed bed can be limited to the deoxygenating stage and the cracking into olefin monomers can be carried out effectively by the conventional steam cracking.

An alternative application of the invention is the one, where the deoxygenation in the fixed bed is followed by catalytic cracking to reduce the molecular mass, whereby the catalysts of the deoxygenation and cracking stages are different from each other. Cracking generates unsaturated hydrocarbons and releases hydrogen, so that the hydrogen-bearing gas exiting them is preferably circulated back to the deoxygenation stage. In that case, it is even possible that the process needs an outer source of hydrogen at the starting stage only and simply works thereafter by the circulated hydrogen.

As the catalyst of cracking that takes place in the fixed bed, acidic catalysts, such as an acidic zeolite catalyst, can be used. As the catalyst of the deoxygenation stage, regardless of the possible catalytic cracking, a metal catalyst, such as NiMo or CoMo can be used. The latter are reduced with hydrogen and treated with hydrogen sulphide in a manner known as such.

With suitable catalysts, the hydrodeoxygenation and a considerable catalytic cracking can take place in the bed simultaneously. Such catalysts include nickel-bearing Y-zeolite (NiY-zeolite) or nickel-bearing montmorolite (NiSMM), which require a high hydrogen pressure in the reactor. NiSMM also cracks resin acids; therefore, it is particularly advantageous for the effective exploitation of the tall oil components.

A suitable reaction temperature at the hydrodeoxygenation stage and the possible catalytic cracking stage is within 330-450° C. At lower temperatures, there is a risk of polymerization and, at higher temperatures, of coking already when feeding the fatty acids into the reactor.

The end products obtained from steam cracking can comprise ethylene and propylene, which can be polymerized into polyethylene or polypropylene. Ethylene can also be used for the production of other polymers, such as polyethylene-terephthalate.

The invention also comprises the fact that bio oil is processed as a partial flow that is combined with crude oil, whereby a result of the final polymerization, correspondingly, is a partially bio-based and partially crude oil-based hybrid polymer. The mixture ratio of bio oil and crude oil in the hydrodeoxygenation and cracking process according to the invention can thus be freely selected.

At first, the invention is described with reference to the appended drawing (FIG. 1), which shows schematically an apparatus intended for the application of the invention.

The basic stages of the hydrodeoxygenation and cracking processes of the fatty acids of a bio oil, such as tall oil, according to the drawing comprise the catalytic deoxygenating and cracking stages 2, 3 that take place in a vertical reactor 1, and the steam cracking of the liquid hydrocarbons obtained from these stages in a separate apparatus 4, which corresponds to the technology known as such in the field of petrochemistry. The feeding 5 of the fatty acids of tall oil, which are separated by distillation and which can include 25% of resin acids maximum, takes place at the upper end of the reactor 1. In addition, hydrogen can be brought to the upper end of the reactor 1 through a line 6. The reactor 1 is filled with quartz wool, which works as bed material 7 and the superimposed, separate zones 2, 3 of which comprise a NiMo catalyst to deoxygenate the acids that were fed and a zeolite catalyst to crack carbon chains. The flow direction of the liquid and gas phases in the reactor 1 is from top to bottom. To adjust the reaction temperatures, the reactor 1 is provided with an electric heater 8.

The hot reaction products exiting through the lower end of the reactor 1 are conducted to a cooler 9, and the liquefied product moves through a line 10 to a separating tank 11, which separates the aqueous phase 12 from the oil phase 13. The oil phase 13, the main component of which typically comprises saturated aliphatic hydrocarbons and which can also contain various amounts of cyclic and aromatic hydrocarbons, unsaturated hydrocarbons and fatty alcohols, moves to steam cracking 4, wherein cracking into low-molecular olefins 14 takes place through several intermediary stages. The olefins are used as starting materials of the production of biopolymers, such as polyethylene or polypropylene.

The gas, which is not condensed in the cooler 9 and which contains hydrogen, oxides of carbon, possibly low-molecular hydrocarbons and other impurities, moves to a purifier 15, which separates hydrogen from the other gas components. Pure hydrogen is circulated through a line 16 back to the upper end of the reactor 1 to constitute the deoxygenating gas, and the oxides of carbon and other impurities 17 are removed from the process.

A simplified implementation of the process according to the invention comprises the fact that the zeolite catalyst 3 in the reactor 1 and, along with that, the catalytic cracking is omitted. In that case, circulating 16 the hydrogen can also be omitted due to the minor amount or lack of hydrogen exiting the reactor. In other respects, the apparatus and the process flow are as illustrated in the drawing.

EXAMPLES

Example tests 1-6, which comprise the hydrodeoxygenation (HDO) and/or catalytic cracking (CC), were carried out on a batch principle as a flow through the reactor without circulating the gas phase. The liquid and gas phases obtained from the reactor were analyzed. In the process according to the invention, the subsequent steam cracking of the organic liquid phase was not carried out, as this technology is well known by those skilled in the art and, on the basis of the analyses, the applicability of the liquid to steam cracking was obvious.

1 g or a zeolite cracking catalyst (ZSM-5) was packed in the vertical reactor pipe inside an electric furnace and, on top of the same, 3 g of a desulphurization/deoxidization catalyst (NiMo with aluminium oxide). The NiMo catalyst was pre-sulphidized by conveying, through the reactor pipe that was packed with catalysts, a hydrogen sulphide-bearing hydrogen flow at a temperature of 393° C. for five hours.

The temperature of the reactor pipe was adjusted to 360° C. and hydrogen gas was conducted through there at 31-32 bar from top to bottom. The hydrogen flow in the reactor was set to about 0.9 g/h. When the flows and temperatures had become even, pumping of a tall oil distillate into the reactor pipe was started in addition to hydrogen, the distillate containing a few resin acids in addition to the fatty acids. The tall oil distillate was fed into the reactor pipe from above, downstream with the flow of hydrogen. The feeding speed of the tall oil distillate was adjusted to 6-9 g/h. Thus, the WHSV (Weight Hourly Space Velocity) with respect to the NiMo catalyst was 2.0-3.0 1/h.

The flow of liquid/gas coming out of the lower end of the reactor was conducted to a pressurized collector tray, which was cooled with cold water. All of the liquid contents of the collector tray were recovered at one-hour intervals. The gas flow exiting the collector tray was conducted outdoors through a decompression valve. The composition of the gas flow was measured at one-hour intervals by an on-line analyzer and the reactor was run for a total of 10 hours.

At the running time of eight hours, whereby the reactor was completely balanced, about 83% of liquid product was recovered from the amount of tall oil distillate that was fed. The liquid product comprised an organic phase and separated water. The liquid product contained a total of 61% hydrocarbons from the amount of the organic phase. The approximate composition of the organic phase comprised: 6% of aromatic hydrocarbons, 42% of saturated hydrocarbons, a total of 10% of unsaturated, aliphatic hydrocarbons and fatty alcohols and 3% of cyclic hydrocarbons. 70% of the saturated hydrocarbons comprised heptadecanes and octadecanes. The gas flow exiting the reactor contained 10% of the reaction products from the amount of tall oil distillate that was fed. The reaction products of the gas flow were: 16% of carbon monoxide, 23% of carbon dioxide, a total of 2% of hydrocarbons C1 and C2, 21% of hydrocarbons C3, 28% of hydrocarbons C4 and a total of 9% of heavier hydrocarbons.

The mass balance measured in the test closed fairly well. The measured mass flows coming out comprised a total of 92% of all the flows fed into the reactor.

The results of tests 1-6 are shown in the following table. The feeding of Tests 1-4 comprised a fatty acid fraction distilled from tall oil (TOFA), which contained 2-5% of fatty acids, that of Test 5 comprised distilled tall oil (DTO), which contained about 25% of resin acids, and that of Test 6 comprised crude tall oil (CTO), which contained a larger amount of resin acids. The Tests 1-3 and 5 were according to the invention, the Tests 4 and 6 were reference tests.

The catalysts for the hydrodeoxygenation stage (HDO) and the catalytic cracking stage (CC) are shown separately.

The lacking of saturated hydrocarbons in Test 4, which comprised the CC stage only, shows an excessive advance of cracking and, thus, the importance of the HDO stage. Tests 5 and 6 show that the resin acids of the starting material increase the portion of aromatics; in Test 6, to an unfavorably high level.

TABLE 1

| | | | Test | | | | | |
|---|---|---|---|---|---|---|---|---|
| | | | 1 | 2 | 3 | 4 | 5 | 6 |
| Feeding | | | TOFA | TOFA | TOFA | TOFA | DTO | CTO |
| Catalyst | HDO | g | 3 | 3 | 3 | | 3 | 3 |
| | CC | g | 2 | 1 | | 2 | 1 | |
| Temperature | | C. | 373 | 369 | 363 | 351 | 368 | 360 |
| WHSV | | | | | | | | |
| with respect to the HDO catalyst | | 1/h | 3.5 | 2.0 | 2.3 | | 2.0 | 2.1 |
| with respect to the CC catalyst | | 1/h | 5.2 | 5.8 | | 3.2 | 6.0 | |
| Hydrogen/feeding | | w/w | 0.07 | 0.15 | 0.20 | 0.16 | 0.16 | 0.20 |
| Liquid product, hydrocarbons | | | | | | | | |
| Approximate yield, % of the liquid feed | | | 105 | 83 | 99 | 80 | 84 | 85 |
| Composition, % from the organic phase: | | | | | | | | |
| Aromatics | | | 21 | 6 | 4 | 9 | 22 | 29 |
| Saturated | | | 30 | 42 | 62 | 0 | 18 | 24 |
| Unsaturated aliphatic/fatty alcohols | | | 8 | 10 | 6 | 6 | 1 | 2 |
| Cyclic | | | 6 | 3 | 1 | 8 | 8 | 7 |
| Hydrocarbons in total | | | 65 | 61 | 73 | 24 | 50 | 60 |
| Gas product, oxides of carbon, hydrocarbons C1-C6 | | | | | | | | |
| Approximate yield, % of the feed | | | | 10 | 2 | 11 | 17 | 5 |
| Composition, % of the gaseous reaction products: | | | | | | | | |
| CO | | | | 16 | 0 | 18 | 12 | 34 |
| CO2 | | | | 23 | 84 | 26 | 20 | 45 |
| C1 + C2 | | | | 2 | 8 | 3 | 3 | 10 |
| C3 | | | | 21 | 0 | 26 | 29 | 3 |
| C4 | | | | 28 | 0 | 21 | 28 | 0 |
| C5 | | | | 8 | 0 | 4 | 6 | 3 |
| C6 | | | | 1 | 0 | 0 | 0 | 0 |
| AcH | | | | 2 | 0 | 1 | 1 | 0 |
| Mass balance | | | | | | | | |
| Outgoing flows, % of the total feed | | | | 92 | 96 | 88 | 97 | 84 |

The invention claimed is:

1. A method of producing olefinic monomers for the production of a polymer, comprising the following stages:
   feeding bio oil and hydrogen gas into a catalyst bed, wherein said bio oil is a fraction separated from crude tall oil, said bio oil consisting of 95% to 98% fatty acids of tall oil and 2% to 5% of resin acids of tall oil;
   catalytically deoxygenating the bio oil by with hydrogen in the catalyst bed in the presence of a deoxygenation catalyst;
   cooling down and dividing a flow exiting the catalyst bed into a hydrocarbon-bearing liquid phase containing at least a portion of aromatics and a hydrogen-bearing gas phase;
   separating water from the hydrocarbon-bearing liquid phase to obtain a hydrocarbon-bearing liquid; and
   subjecting the hydrocarbon-bearing liquid containing said at least a portion of aromatics to stream cracking to form a product containing olefinic monomers.

2. The method according to claim 1, wherein the deoxygenation catalyst is metallic.

3. The method according to claim 1, wherein the catalyst bed is a fixed bed formed by fixed bed material.

4. The method according to claim 3, wherein, in the fixed bed, the deoxygenation is followed by a catalytic cracking stage and wherein the deoxygenation catalyst and a cracking catalyst are used, which are different from each other.

5. The method according to claim 4, wherein the catalyst of the cracking stage is acidic.

6. The method according to claim 4 or 5, wherein the catalysts of the deoxygenation and cracking stage are located successively and spaced apart in the fixed bed formed by the fixed bed material.

7. The method according to claim 1, wherein the catalyst of the deoxygenation and/or the cracking stage is a nickel-bearing silicate.

8. The method according to claim 1, wherein the bio oil and hydrogen gas flow in the catalyst bed from top to bottom.

9. The method according to claim 1, wherein the hydrogen-bearing gas phase is separated from the hydrogen-bearing liquid phase and is circulated back to constitute a feeding gas of a deoxygenation stage.

10. The method according to claim 1, wherein the hydrocarbons in the hydrocarbon-bearing liquid phase and the hydrocarbon-bearing liquid are in the boiling range of naphtha.

11. The method according to claim 1, wherein ethylene and/or propylene are produced by the steam cracking.

12. The method according to claim 2, wherein the metallic deoxygenation catalyst is a NiMo catalyst or a CoMo catalyst.

13. The method according to claim 5, wherein the acidic catalyst of the cracking stage is an acidic zeolite catalyst.

14. The method according to claim 7, wherein the nickel-bearing silicate is nickel-substituted montmorillonite.

15. The method according to claim 1, wherein the content of the bio oil is at least 95% oleic acid and linoleic acid.

* * * * *